US012766227B2

(12) United States Patent
Powner et al.

(10) Patent No.: US 12,766,227 B2
(45) Date of Patent: Oct. 20, 2026

(54) OSTOMY POUCHES

(71) Applicant: SALTS HEALTHCARE LIMITED, Birmingham (GB)

(72) Inventors: Iain Powner, Birmingham (GB); Lee Tretheway, Birmingham (GB); Andrew Barron, Swansea (GB); Donald Hill, Swansea (GB); Shirin Alexander, Swansea (GB)

(73) Assignee: SALTS HEALTHCARE LIMITED, Birmingham (GB)

( * ) Notice: Subject to any disclaimer, the term of this patent is extended or adjusted under 35 U.S.C. 154(b) by 1085 days.

(21) Appl. No.: 17/598,109

(22) PCT Filed: Mar. 25, 2020

(86) PCT No.: PCT/GB2020/050790
§ 371 (c)(1),
(2) Date: Sep. 24, 2021

(87) PCT Pub. No.: WO2020/201718
PCT Pub. Date: Oct. 8, 2020

(65) Prior Publication Data

US 2022/0184281 A1 Jun. 16, 2022

(30) Foreign Application Priority Data

Mar. 29, 2019 (GB) ...................................... 1904455

(51) Int. Cl.
*A61L 28/00* (2006.01)
*A61F 5/44* (2006.01)
*A61F 5/445* (2006.01)

(52) U.S. Cl.
CPC ........ *A61L 28/0061* (2013.01); *A61F 5/4405* (2013.01); *A61F 5/445* (2013.01);
(Continued)

(58) Field of Classification Search
CPC ............. A61L 28/0007; A61L 28/0034; A61L 28/0061; A61L 2420/04; A61L 2400/10;
(Continued)

(56) References Cited

U.S. PATENT DOCUMENTS 5,271,987 A 12/1993 Iskra
5,591,144 A 1/1997 Smith et al.
(Continued)

FOREIGN PATENT DOCUMENTS

CN 102665618 A 9/2012
CN 105358322 A 2/2016
(Continued)

OTHER PUBLICATIONS

Office Action for co-pending U.S. Appl. No. 17/598,066 issued Nov. 19, 2024, 8 pages.
(Continued)

*Primary Examiner* — Rebecca E Eisenberg
*Assistant Examiner* — Timothy L Flynn
(74) *Attorney, Agent, or Firm* — Leydig, Voit & Mayer, Ltd.

(57) ABSTRACT

An ostomy pouch has a pair of opposed side walls, one of the side walls defines a stoma-receiving opening for, in use, receiving a part of a stoma into the ostomy pouch, one or both of the side walls being formed of a polymeric film at least partially coated on an internal surface thereof with hydrophobic particles, the hydrophobic particles includes: a metal oxide core; and a hydrocarbon chain having from 2 to 40 carbon atoms, wherein the hydrocarbon chain is chemically bound to the metal oxide core.

19 Claims, 5 Drawing Sheets

(52) U.S. Cl.
CPC ....... *A61L 28/0007* (2013.01); *A61L 28/0034* (2013.01); *A61L 2420/04* (2013.01)

(58) Field of Classification Search
CPC ........ A61L 2400/12; A61F 5/44; A61F 5/445; A61F 5/4405; A61F 2310/00395; A61F 2310/00598
See application file for complete search history.

(56) References Cited

U.S. PATENT DOCUMENTS

| | | | | |
|---|---|---|---|---|
| 5,855,571 | A | 1/1999 | Steger et al. | |
| 8,598,406 | B2 | 12/2013 | Ponomarenko et al. | |
| 2001/0044378 | A1 | 11/2001 | Steer et al. | |
| 2002/0133225 | A1 | 9/2002 | Gordon | |
| 2003/0148684 | A1 | 8/2003 | Cramer et al. | |
| 2005/0008839 | A1 | 1/2005 | Cramer et al. | |
| 2005/0065485 | A1* | 3/2005 | Andersen | A61F 5/445 604/332 |
| 2006/0159916 | A1* | 7/2006 | Dubrow | B01J 20/3219 428/401 |
| 2006/0258999 | A1 | 11/2006 | Ponomarenko et al. | |
| 2007/0003463 | A1 | 1/2007 | Ajiri | |
| 2008/0268233 | A1 | 10/2008 | Lawin et al. | |
| 2009/0304991 | A1 | 12/2009 | Tanioka et al. | |
| 2011/0125114 | A1 | 5/2011 | Bekele | |
| 2012/0275009 | A1 | 11/2012 | Vermeulen et al. | |
| 2012/0308662 | A1 | 12/2012 | Konishi et al. | |
| 2012/0308823 | A1 | 12/2012 | Ajiri | |
| 2013/0081555 | A1 | 4/2013 | Li | |
| 2014/0330229 | A1 | 11/2014 | Lee | |
| 2015/0175317 | A1* | 6/2015 | Imai | B32B 27/08 428/323 |
| 2015/0175814 | A1* | 6/2015 | Aizenberg | C09D 5/1693 427/2.24 |
| 2016/0075883 | A1 | 3/2016 | Ebert et al. | |
| 2016/0130487 | A1 | 5/2016 | Iwamoto et al. | |
| 2017/0015843 | A1 | 1/2017 | Liu et al. | |
| 2017/0189895 | A1 | 7/2017 | Hatakeyama et al. | |

FOREIGN PATENT DOCUMENTS

| | | | |
|---|---|---|---|
| CN | 107189656 | A | 9/2017 |
| CN | 109251345 | A | 1/2019 |
| DE | 102014218355 | A1 | 3/2016 |
| EP | 0593219 | A2 | 4/1994 |
| EP | 2858492 | B1 | 4/2015 |
| EP | 3017942 | B1 | 5/2016 |
| GB | 2273052 | A | 6/1994 |
| GB | 2510563 | A | 8/2014 |
| GB | 2534012 | A | 7/2016 |
| JP | 2008-266050 | A | 11/2008 |
| JP | 2017/170739 | A | 9/2017 |
| JP | 2018-192162 | A | 12/2018 |
| WO | WO 2007/029293 | A1 | 3/2007 |
| WO | WO 2012/173803 | A1 | 12/2012 |
| WO | WO 2014/019809 | A1 | 2/2014 |
| WO | WO 2014/192402 | A1 | 12/2014 |
| WO | WO 2017/075333 | A1 | 5/2017 |
| WO | WO 2018/041320 | A2 | 3/2018 |
| WO | WO 2018/085376 | A2 | 5/2018 |

OTHER PUBLICATIONS

Examination Report under Section 18(3) by UK Intellectual Property Office issued May 9, 2022, regarding Application No. GB1904458.5, 2 pages.
1st Office Action issued Nov. 16, 2022, for Chinese Patent Application No. 202080025833.7, 11 pages.
Office Action with English Translation for JP Patent Application No. 2021-558526 issued Dec. 12, 2023, 4 pages.
U.S. Appl. No. 17/598,066, filed Sep. 24, 2021, Pending.
European Patent Office Communication of a Notice of Opposition issued May 3, 2023, for European Patent No. 3946179, European Patent Application No. 20716885.7, 23 pages.
International Search Report and Written Opinion associated with International application No. PCT/GB2020/050790, issued May 29, 2020, 9 pages.
International Search Report and Written Opinion associated with International application No. PCT/GB2020/050789, issued Jun. 16, 2020, 11 pages.
Al-Shatty et al. (Jun. 6, 2017) "Tunable Surface Properties of Aluminum Oxide Nanoparticles from Highly Hydrophobic to Highly Hydrophilic" *ACS Omega* 2(6): 2507-2514; DOI: 10.1021/acsomega.7b00279.
Alexander et al. (Dec. 7, 2015) "Branched Hydrocarbon Low Surface Energy Materials for Superhydrophobic Derived Surfaces" *ACS Applied Materials & Interfaces* 8(1): 660-666; DOI: 10.1021/acsami.5b09784.
Ebert et al. (Jul. 5, 2012) Transparent, superhydrophobic, and wear-resistant coatings on glass and polymer substrates using SiO2, ZnO, and ITO nanoparticles. *Langmuir*. 28(31): 11391-11399. doi:10.1021/la301479c.
Haas et al. (Jan. 1, 2000) "Hybrid Inorganic-Organic Polymers Based on Organically Modified Si-Alkoxides" *Adv. Eng. Mater*. 2(9): 571-582; Retrieved from the Internet: URL:http://www3.interscience.wiley.com/cgi-bin/issn?DESCRIPTOR=PRINTISSN&VALUE=1438-1656.
Hill et al. (Jan. 30, 2020) "Controlling the wettability of plastic by thermally embedding coated aluminium oxide nanoparticles into the surface" *J Colloid Interface Sci*. 567: 45-53. doi:10.1016/j.jcis.2020.01.116.
Search Report under Section 17(5) by UK Intellectual Property Office issued Sep. 25, 2019 regarding Application No. GB1904455.1, 3 pages.
Search Report under Section 17(5) by UK Intellectual Property Office issued Nov. 29, 2019 regarding Application No. GB1904458.5, 5 pages.
Prontera et al. (Jul. 11, 2019) "Sustainable, Fluorine-Free, Low Cost and Easily Processable Materials for Hydrophobic Coatings on Flexible Plastic Substrates" *Materials* (*Basel*) 12(14): 2234 (11 pages). doi:10.3390/ma12142234.
Evonik Industries AG, Product Information for Aerosil® R 805, Aug. 2013, 2 pp.
Evonik Industries AG, Product Information for Aeroxide® Alu C 805, Aug. 2013, 2 pp.
Evonik Industries AG, Product Information for Aeroxide® TiO2 T 805, Jul. 2015, 2 pp.
Bauer et al. (2008) "Improved attachment of mesenchymal stem cells on super-hydrophobic TiO2 nanotubes" Acta Biomaterialia 4:1576-1582; https://doi.org/10.1016/j.actbio.2008.04.004.
Examination report for IN Patent Application No. 202127043136 issued Jan. 23, 2026, 7 pp.

* cited by examiner

OSTOMY POUCHES

CROSS-REFERENCE TO RELATED APPLICATIONS

This application is a U.S. National Stage Application filed under 35 U.S.C. § 371 of International Application No. PCT/GB2020/050790, filed Mar. 25, 2020, which claims the benefit of Great Britain Application No. 1904455.1, filed Mar. 29, 2019. Both of these applications are hereby incorporated by reference in their entireties.

FIELD

This specification relates to ostomy pouches and, in particular, to ostomy pouches where at least a portion of an inner surface thereof is coated with hydrophobic particles to result in the inner surface having a water contact angle (WCA) of approximately 140° or greater. The hydrophobic particles disclosed herein are non-toxic and adhere well to polymeric films. Accordingly, the hydrophobic particles disclosed herein are particularly well suited for use in ostomy.

BACKGROUND

Ostomy pouches are medical devices that provide a means for the collection of body waste from a stoma. Ostomy pouches are most commonly associated with colostomies, ileostomies and urostomies. Ostomy pouches typically comprise a collection bag and a baseplate (also known as a flange or a wafer). There are one-piece ostomy pouches where the collection bag and baseplate are supplied as a single item and there are two-piece ostomy pouches where the collection bag and baseplate are supplied as separate items for attaching to one another.

Ostomy pouches can be further divided into two basic types: open-end pouches and closed-end pouches. Open-end pouches typically comprise a drainable opening for the removal of body waste, e.g. into a toilet. The drainable opening may include a valve or the drainable opening may be opened and closed using a clip or a hook and loop fastener. Closed-end pouches are typically removed from the patient when full. The closed-end pouch may then be disposed of or emptied and cleaned ready for re-use.

Ostomy pouches, particularly closed-end pouches, can suffer from the phenomenon of pancaking. This is where a vacuum occurs within the pouch and the internal surfaces of the side walls stick together. Consequently, the body waste is prevented from falling to the bottom of the bag. The trapped body waste can contaminate adhesive on the baseplate which can result in the ostomy pouch becoming detached from the patient.

Open-end pouches can be problematic when the drainable opening gets trapped with body waste. In such circumstances the open-end pouch can be challenging to drain and may need to be removed to clean thoroughly. In certain circumstances, however, it may not be possible to sufficiently clean the drainable opening which can mean that the open-end pouch needs to be replaced.

It is known to use hydrophobic materials to create surfaces that are difficult to wet, non-stick, self-cleanable and/or resistant to contamination. Such hydrophobic materials typically include waxes, fluorinated polymers, e.g. polytetrafluoroethylene (PTFE), organosilanes, etc.

However, known hydrophobic materials are not always suitable for use in ostomy because often they do not adhere well to polymeric films and/or they can be toxic, e.g. fluorine-containing.

There is a commercial need for improved ostomy pouches that seek to overcome the above-described problems.

SUMMARY OF INVENTION

Embodiments of the present invention seek to provide ostomy pouches that are simple and quick to clean, address the issues of pancaking and drainage, whilst at the same time are durable and non-toxic.

According to a first aspect of the invention, there is provided an ostomy pouch having a pair of opposed side walls, one of the side walls defining a stoma-receiving opening for, in use, receiving a part of a stoma, one or both of the side walls being formed of a polymeric film at least partially coated on an internal surface thereof with hydrophobic particles, the hydrophobic particles comprising:

a metal oxide core; and a hydrocarbon chain having from 2 to 40 carbon atoms, wherein the hydrocarbon chain is chemically bound to the metal oxide core.

The side wall defining the stoma-receiving opening may be formed of the polymeric film and may comprise a first region which at least partially surrounds or surrounds the stoma-receiving opening, wherein the first region is coated with the hydrophobic particles.

The first region may have a peripheral edge located approximately 20 mm to approximately 80 mm (such as from approximately 20 mm to approximately 60 mm, e.g. 40 mm) from the centre of the stoma-receiving opening.

The side wall opposing the side wall defining the stoma-receiving opening may be formed of the polymeric film and may comprise a second region which substantially faces the stoma-receiving opening, wherein the second region is coated with the hydrophobic particles.

The diameter of the second region may be greater than the diameter of the stoma-receiving opening.

The diameter of the second region may be greater than, less than or approximately equal to the diameter of the first region.

The ostomy pouch may comprise a drainable opening at a lower end thereof, both side walls being formed of the polymeric film and comprising a third region which surrounds the drainable opening, wherein the third region is coated with the hydrophobic particles.

The drainable opening may include a valve for controlling the flow of body waste therefrom.

The internal surface of the valve may be coated with the hydrophobic particles.

Both side walls may be formed of the polymeric film and the entire internal surfaces thereof may be coated with the hydrophobic particles.

The average diameter of the hydrophobic particles may be less than or equal to approximately 200 nm.

The average diameter of the hydrophobic particles may be less than or equal to approximately 50 nm, e.g. less than or equal to approximately 20 nm.

The average diameter of the hydrophobic particles may be from approximately 8 nm to approximately 20 nm, such as from approximately 8 nm to approximately 15 nm.

The metal oxide core may comprise one or a combination of aluminium oxide, iron oxide, zinc oxide, and silicon oxide.

The hydrocarbon chain may be aliphatic.

The hydrocarbon chain may be straight or branched.

The hydrocarbon chain may have from 2 to 32 carbons.

The hydrocarbon chain may have from 6 to 32 carbons, such as from 6 to 24 carbons.

The hydrocarbon chain may be covalently bound to the metal oxide core via a functional group, e.g. an anionic functional group.

The functional group may comprise any one or a combination of hydroxide, carboxylate, phosphonate, phosphinate, thiolate and thiocarboxylate.

The hydrophobic particles may be free from fluorine.

The polymeric film may comprise a thermoplastic film. For instance, the polymeric film may comprise any one or more of a polyolefin, vinyl polymer, polyester and polyacetal film.

The polymeric film may comprise a co-extruded bilayer or multilayer film. For instance, the co-extruded bilayer or multilayer film may comprise layers of any one or a combination of polyethylene (PE), polypropylene (PP), acetal, acrylic, polyamide, polyvinyl chloride (PVC), ethylene vinyl acetate (EVA), polyvinylidene chloride (PVDC), polystyrene (PS), acrylonitrile butadiene styrene (ABS) and polycarbonate (PC).

The hydrophobic particles may be deposited (e.g. sprayed) onto the polymeric film. For instance, the hydrophobic particles may be mixed with a carrier, such as a volatile solvent, and the resultant mixture may be sprayed onto the polymeric film. The mixture of the hydrophobic particles and the carrier may form a solution or suspension. The mixture may have a hydrophobic particle concentration of from approximately 0.5 wt % to approximately 20 wt %, such as from approximately 0.5 wt % to approximately 10 wt %, such as from approximately 0.5 wt % to approximately 5 wt %, e.g. 0.5 wt % or 1 wt % or 2 wt % or 3 wt % or 4 wt % or 5 wt %.

The hydrophobic particles may be at least partially embedded in the polymeric film.

The polymeric film may be heated to enable the hydrophobic particles to become at least partially embedded therein to form a hydrophobic three-dimensional surface. Embedding of the hydrophobic particles may be enhanced by physical means, such as by rolling the heated polymeric film between rollers. During processing, the volatile solvent (where used) naturally evaporates and as the polymeric film cools the hydrophobic particles remain bound to the polymeric film such that they are not removed by washing.

The temperature to which the polymeric film is heated will vary depending on the type of polymeric film being utilised. In general, the polymeric film is heated to a temperature at which it starts to deform plastically. It is to be appreciated that the skilled person will know this temperature or will be able to determine this temperature through basic experimentation. For the EVA/EVA/PVDC/EVA/EVA five layer co-extruded thermoplastic film utilised in the below examples, the plastics deformation temperature was between approximately 80° C. and approximately 90° C.

The hydrophobic particles and the polymeric film may be secured to one another by an adhesive, such as an epoxy resin. For instance, an adhesive may be deposited onto the polymeric film followed by the hydrophobic particles. Alternatively, the hydrophobic particles may be deposited onto the polymeric film followed by the adhesive. The hydrophobic particles may become at least partially embedded in the polymeric film, which itself provides the bond between the polymeric film and the hydrophobic particles. When the adhesive is cured, the result is a polymeric film having a hydrophobic three-dimensional surface.

The hydrophobic particles and the adhesive may be mixed and the resultant mixture may be deposited onto the polymeric film.

Where the hydrophobic particles and the adhesive are mixed, the mass ratio of the hydrophobic particles and the adhesive may be from approximately 1.0:1.0 to approximately 2.0:1.0. Mass ratios of hydrophobic particles and adhesive in this range have been found to produce polymeric films having particularly good hydrophobic surfaces, particularly where the metal oxide core comprises aluminium oxide.

The hydrophobic particles or the hydrophobic particle/adhesive mixture may be sprayed onto the polymeric film using a carrier, e.g. a volatile solvent, as described previously.

In all methods of attaching the hydrophobic particles to the polymeric film it has been found that the WCAs are not adversely affected even after the polymeric film has been immersed in or exposed to a solvent. Such treatment may result in some of the hydrophobic particles becoming removed from the polymeric film but the removal has a negligible effect on the WCA.

The hydrophobicity of the polymeric film may be tuned at different regions across the surface thereof. By this it is meant that a first region of the polymeric film may have an associated first WCA measurement and a second (or further) region of the polymeric film may have an associated second WCA measurement which differs from the first WCA measurement.

Tuning the hydrophobicity of the polymeric film may be achieved in a number of ways. For instance, more layers of hydrophobic particles may be deposited at the first region than at the second region. Accordingly, the first region will typically have a higher WCA measurement than the second region. Additionally or alternatively, a more concentrated mixture of hydrophobic particles may be deposited at the first region than at the second region. Accordingly, the first region will typically have a higher WCA measurement than the second (or further) region. The concentration of hydrophobic particles in the mixture may be adjusted by dilution with the solvent and/or a different species, e.g. a hydrophilic particle and/or an unfunctionalised metal oxide. Additionally or alternatively, different types of hydrophobic particles may be deposited at the respective first and second regions. Accordingly the first and second regions will typically have differing WCA measurements.

The present invention provides ostomy pouches formed from self-cleaning polymeric films. At least a portion of the inside surface of the ostomy pouch has a hydrophobic surface formed by securing hydrophobic particles to a polymeric film.

The methods of attaching the hydrophobic particles to the polymeric film result in a polymeric film having a three-dimensional surface structure which can achieve a WCA of approximately 140° or greater. Accordingly, ostomy pouches of the invention can offer improved self-cleaning properties, be resistant to contamination and/or be easier to clean. Ostomy pouches of the present invention are also considered to be more durable in terms of these properties and, hence longer living, when compared to known ostomy pouches due to improved adhesion between the hydrophobic particles and the polymeric film.

BRIEF DESCRIPTION OF THE FIGURES

Embodiments will now be described by way of example only with reference to the accompanying drawings, in which.

DESCRIPTION OF EMBODIMENTS

Figure 1:
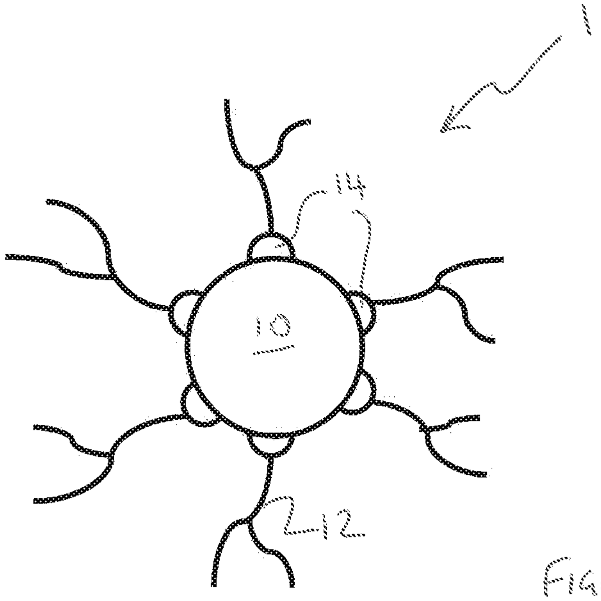
FIG. 1 is a representation of a hydrophobic particle.

Referring to FIG. 1 there is shown a hydrophobic particle, represented generally at 1. The hydrophobic particle 1 comprises a metal oxide core 10 and six hydrocarbon chains 12. It is to be appreciated that in other embodiments the hydrophobic particle 1 may have greater than or less than six hydrocarbon chains 12. Each hydrocarbon chain 12 has from 2 to 40 carbon atoms. The hydrocarbon chains 12 are branched, although they could be straight.

The hydrocarbon chains 12 are chemically bound to the metal oxide core 10. In some embodiments, the hydrocarbon chains 12 may be covalently bound to the metal oxide core 10 via a functional group 14. Suitable metal oxide cores 10 include aluminium oxide, iron oxide, zinc oxide, and silicon oxide.

The term "oxide" as used herein is intended to include oxide-hydroxides, hydroxides and also oxides having multiple metal oxidation states. For example, iron oxide may include $Fe_3O_4$ or $Fe_2O_3$ or a combination thereof.

In some embodiments, the hydrophobic particle 1 comprises a metal oxide core 10 having a hydrocarbon chain 12 covalently bound thereto by a carboxylate functional group 14. In other embodiments, alternative functional groups may be employed as long as a stable covalent interaction is formed between the metal oxide core 10 and the hydrocarbon chain 12. Alternative functional groups 14 may comprise any one or a combination of hydroxide, phosphonate, phosphinate, thiolate and thiocarboxylate.

In some embodiments, the hydrocarbon chain 12 may be aliphatic. In particular, the hydrocarbon chain 12 may be chosen from any suitable alkyl organic group as defined by the formula $C_xH_y$, where x and y are whole numbers and x is from 2 to 40. In some embodiments, the hydrocarbon chain 12 may have from 6 to 32 carbons, such as from 6 to 24 carbons.

In some embodiments, the hydrocarbon chain 12 may be straight. For instance, the hydrophobic particle 1 may be created by reaction of octanoic acid ($CH_3(CH_2)_6CO_2H$) with the metal oxide core 10.

In some embodiments, the hydrocarbon chain 12 may be branched. For instance, the hydrophobic particle 1 may be created by reaction of any one of isostearic acid ($CH_3(CH_2)_{16}COOH$) and 2-hexyldecanoic acid ($CH_3(CH_2)_7CH[(CH_2)_5CH_3]CO_2H$) with the metal oxide core 10.

Creation of the hydrocarbon chains 12 as described herein can provide the advantage that the resultant hydrophobic particles 1 are free from fluorine. This means that the hydrophobic particles 1 of the invention have environmental benefits in that they are less toxic when compared to prior art materials.

Figure 2:
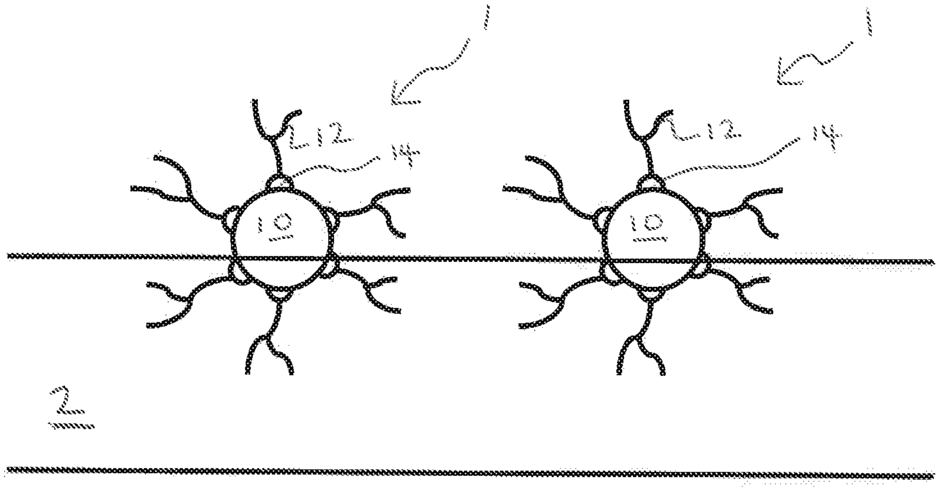
FIG. 2 shows a polymeric film having hydrophobic particles at least partially embedded therein.

Referring now to FIG. 2, there is shown a polymeric film 2 having the hydrophobic particles 1 at least partially embedded therein.

In some embodiments, the polymeric film 2 is prepared by depositing, e.g. spraying, the hydrophobic particles 1 onto a heated surface thereof. The hydrophobic particles 1 may be dissolved or suspended in a solvent. The exposed surface of the polymeric film 2 may be heated until it is softened, followed by deposition of the solution or suspension onto the softened surface. After allowing the solvent to evaporate and the surface to cool the hydrophobic particles 1 become at least partially embedded in the polymeric film 2. The result is a polymeric film 2 having a stable, textured and hydrophobic surface. In some embodiments, the polymeric film 2 may be heated by radiation (for example, by infra-red lamps) or by conduction (for example, by placing the polymeric film 2 on a hot plate or by exposing to heated air). It is to be understood that any method that provides sufficient heating to soften the polymeric film 2 without compromising its integrity may be employed.

The choice of solvent is limited only by the need for the solvent to evaporate from the surface of the polymeric film 2. Suitable solvents include, but are not limited to, isopropanol, toluene and ethanol.

Figure 3:
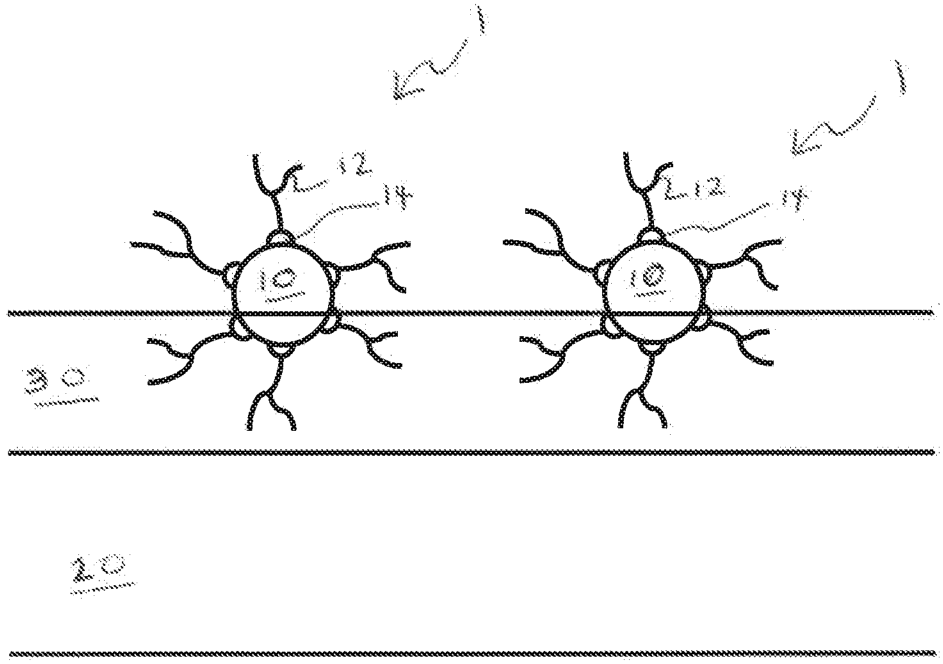
FIG. 3 shows a polymeric film comprising hydrophobic particles bonded thereto by an adhesive.

Referring now to FIG. 3, there is shown a polymeric film 20 where the hydrophobic particles 1 are secured thereto by an adhesive 30.

In some embodiments, the adhesive 30 may be an epoxy resin. The adhesive 30 may be applied to the polymeric film 20, followed by deposition of the solution or suspension containing the hydrophobic particles 1, or vice versa. The adhesive 30 is allowed to cure, at which point the hydrophobic particles 1 become bonded to the polymeric film 20 by virtue of being at least partially embedded in the adhesive 30.

In some embodiments, the hydrophobic particles 1 and the adhesive 30 may be mixed and the resultant mixture may be deposited, e.g. sprayed, onto the polymeric film 20.

Spraying may be effected by dissolving or suspending the mixture in a solvent and utilising a propellant or a compressor as is well known in the industry.

Materials

The polymeric film may comprise a thermoplastic film, e.g. a polyethylene copolymer. The polymeric film used for all of the subsequent experiments was an EVA/EVA/PVDC/EVA/EVA five layer co-extrusion having a thickness of 75 micron.

Aluminium oxide ($Al_2O_3$) particles having an average diameter of 13 nm were purchased from Sigma-Aldrich.

Iron oxide ($Fe_3O_4$) particles having an average diameter of from 15-20 nm were purchased from Sigma-Aldrich.

Isostearic acid was purchased from Nissan Chemical Industries and was used without further purification.

Toluene and isopropanol were supplied by VWR Chemicals.

SP106 Multi-Purpose Epoxy Resin System 1 kg Slow Hardener was purchased from MB Fibreglass.

Spraycraft Universal Airbrush Propellant was used for the spray coating and was purchased from Axminster Tools and Machinery.

Water Contact Angle (WCA) Measurements

WCA measurements were used to study the wettability of the polymeric films. WCA measurements were obtained by depositing 4 μL droplets of $H_2O$ onto the polymeric films. The values of the WCAs that are reported herein are the average of three measurements, recorded at different positions on the surfaces. Standard deviations are used to represent the uncertainties that are associated with these values.

COMPARATIVE EXAMPLE 1

The WCA of the uncoated polymeric film (i.e. the clean EVA/EVA/PVDC/EVA/EVA five layer co-extruded film) was 88.3°±1.7°.

COMPARATIVE EXAMPLE 2

The polymeric film was coated with unfunctionalised $Al_2O_3$ particles. Deposition of the unfunctionalised $Al_2O_3$ particles onto the polymeric film was achieved through spray coating from 2% wt isopropanolic suspensions at ambient temperature. Three sprays were used to try to achieve maximum coverage of the polymeric film by the unfunctionalised $Al_2O_3$ particles.

Coating the polymeric film with the unfunctionalised $Al_2O_3$ particles at ambient temperature resulted in the surface thereof becoming superhydrophilic. Accordingly, it was not possible to accurately measure the WCA of the resultant polymeric film.

COMPARATIVE EXAMPLE 3

The polymeric film was coated with unfunctionalised $Fe_3O_4$ particles. Deposition of the unfunctionalised $Fe_3O_4$ particles onto the polymeric film was achieved through spray coating from 2% wt isopropanolic suspensions at ambient temperature. Three sprays were used to try to achieve maximum coverage of the polymeric film by the unfunctionalised $Fe_3O_4$ particles.

The WCA of the resultant polymeric film was 107.2°±3.4°.

EXAMPLE 1

Functionalised aluminium oxide ($Al_2O_3$) particles were synthesised as follows. Aluminium oxide ($Al_2O_3$) particles (d=13 nm, 10.0 g, 98.0 mmol, 1.0 equiv.) were refluxed with isostearic acid (39.1 g, 137.3 mmol, 1.4 equiv.) in toluene (250 mL) for 24 hours. Once the reaction time had elapsed, the reaction mixture was collected and centrifuged at 5000 rpm for one hour. The solid was then recovered and centrifuged at 5000 rpm in isopropanol for one hour. Following this, the solid was centrifuged in ethanol at 5000 rpm for one hour three further times, and then dried at 80° C. for six hours.

The polymeric film was coated with the functionalised $Al_2O_3$ particles. Deposition of the functionalised $Al_2O_3$ particles onto the polymeric film was achieved through spray coating from 2% wt isopropanolic suspensions at ambient temperature. Three sprays were used to try to achieve maximum coverage of the polymeric film by the functionalised $Al_2O_3$ particles.

The WCA of the resultant polymeric film was 151.1°±1.0°.

EXAMPLE 2

Functionalised iron oxide ($Fe_3O_4$) particles were synthesised as follows. Iron oxide ($Fe_3O_4$) particles (d=15-20 nm, 5.0 g, 21.6 mmol, 1.0 equiv.) were refluxed in toluene (100 mL) with isostearic acid (18.4 g, 64.7 mmol, 3.0 equiv.) for approximately twenty-four hours, under mechanical stirring. Once the reaction time had elapsed, the mixture was centrifuged at 5000 rpm for one hour. Following this, the solid was recovered and dried at 80° C. for six hours.

The polymeric film was coated with the functionalised $Fe_3O_4$ particles. Deposition of the functionalised $Fe_3O_4$ particles onto the polymeric film was achieved through spray coating from 2% wt isopropanolic suspensions at ambient temperature. Three sprays were used to try to achieve maximum coverage of the polymeric film by the functionalised $Fe_3O_4$ particles.

The WCA of the resultant polymeric film was 151.9°±2.1°.

EXAMPLE 3

The polymeric film was heated and coated with the functionalised $Al_2O_3$ particles described in Example 1. The functionalised $Al_2O_3$ particles were spray coated onto the polymeric film once it had been softened as a result of heating. Heating of the polymeric film was accomplished as follows. First, the polymeric film was physically attached at its edges to the surface of a glass petri dish. The purpose of this was to secure the polymeric film in order to limit the extent to which it changed shape during the heating process. Heat was then applied to the petri dish until physical deformation of the polymeric film was observed. Once physical deformation of the polymeric film was observed, deposition of the functionalised $Al_2O_3$ particles onto the polymeric film was achieved through spray coating. The functionalised $Al_2O_3$ particles were spray coated from a 2.0% wt suspension. Five sprays were used to try to achieve maximum coverage of the polymeric film by the functionalised $Al_2O_3$ particles. Following each spray, the polymeric film was continually heated in order to accelerate the removal of the isopropanol. Further spray coating was performed on the polymeric film when no liquid was observed its surface. The temperature of the polymeric film was not measured prior to spray coating. However, it was observed that the polymeric film would start to deform plastically when heated to between 80-90° C.

The WCA of the resultant polymeric film was 142.0°±3.9°.

Although this value is slightly lower than when the functionalised $Al_2O_3$ particles were deposited onto the polymeric film at ambient temperature (Example 1), it is noteworthy that water droplets would readily roll off the coated polymeric film. Accordingly, this suggests that heating of the polymeric film during application of the hydrophobic particles does not overly detriment the desired hydrophobic nature of the resultant polymeric film.

In order to determine how well the functionalised $Al_2O_3$ hydrophobic particles bonded the polymeric film was sonicated in isopropanol for approximately ten minutes and the WCA was retested.

Following sonication, the WCA of the polymeric film was 137.7°±7.9°. It is evident that the WCA did not change significantly following sonication which indicates a strong thermal embedding of the functionalised $Al_2O_3$ hydrophobic particles within the polymeric film.

EXAMPLE 4

The polymeric film was heated and coated with the functionalised $Fe_3O_4$ particles described in Example 2 according to the method described in Example 3.

The WCA of the resultant polymeric film was 151.9°±2.7°.

In order to determine how well the functionalised $Fe_3O_4$ hydrophobic particles bonded the polymeric film was sonicated in isopropanol for approximately ten minutes and the WCA was retested.

Following sonication, the WCA of the polymeric film was 90.3°±0.5°. This represents a WCA close to that of the uncoated polymeric film. This indicates that most of the functionalised $Fe_3O_4$ hydrophobic particles were removed by the sonication. Without being bound to any particular theory, it is understood that functionalised $Fe_3O_4$ hydrophobic particles form relatively large agglomerates on the surface that are less strongly embedded than, say, functionalised $Al_2O_3$ hydrophobic particles. Accordingly, the functionalised $Fe_3O_4$ hydrophobic particles are more easily removed than the functionalised $Al_2O_3$ hydrophobic particles. However, that is not to say that embodiments incorporating functionalised $Fe_3O_4$ hydrophobic particles are not commercially viable. The sonication test merely seeks to replicate a highly destructive environment to determine the degree of bonding between the hydrophobic particles and the polymeric film. Hydrophobic films are unlikely to experience such a highly destructive environment in normal use.

EXAMPLES 5 TO 9

Bonding of the functionalised $Al_2O_3$ particles and the polymeric film by an epoxy resin was studied in examples 5 to 9.

In example 5, 0.08 g of epoxy resin was added to 0.66 g of the functionalised $Al_2O_3$ particles described in Example 1 and suspended in 40 mL of isopropanol, such that the mass ratio of functionalised $Al_2O_3$ particles:epoxy resin was approximately 8.6:1.0. Deposition of the mixture onto the polymeric film was performed through spray coating at ambient temperature, as described previously. Spray coating this suspension onto the polymeric film resulted in a polymeric film having a WCA of 144.3°±4.3°.

In examples 6 to 9, the ratio of the functionalised $Al_2O_3$ particles and epoxy resin was adjusted.

The functionalised $Al_2O_3$ particle and epoxy resin ratios and the corresponding WCAs for the polymeric films of examples 5 to 9 are summarised in Table 1. Table 1 also shows the WCAs for the polymeric films after they have been sonicated in isopropanol for approximately ten minutes.

TABLE 1

Water contact angle (°) before and after sonication as a function of the ratio of functionalised $Al_2O_3$ particles and epoxy resin.

| Example | Functionalised $Al_2O_3$ particles:epoxy resin | Water contact angle (°) | Water contact angle (°) after sonication |
|---|---|---|---|
| 5 | 8.6:1.0 | 144.3 ± 4.3° | 132.2 ± 7.4° |
| 6 | 2.0:1.0 | 149.9 ± 1.1° | 137.1 ± 1.0° |
| 7 | 1.5:1.0 | 150.7 ± 1.2° | 135.9 ± 7.5° |
| 8 | 1.0:1.0 | 149.0 ± 7.8° | 141.1 ± 1.6° |
| 9 | 1.0:1.4 | 138.1 ± 10.4° | 142.0 ± 0.6° |

Whilst all of examples 5 to 9 achieved high WCAs, it is clear that polymeric films with the best hydrophobicity were created when the ratio of the functionalised $Al_2O_3$ particles and epoxy resin was from approximately 1.0:1.0 (i.e. 149.0±7.8°) to approximately 2.0:1.0 (i.e. 149.9±1.1°), e.g. 1.5:1.0 (i.e. 150.7±1.2°).

Moreover, as with Example 3, it is evident that the WCAs of Examples 5 to 9 did not change significantly following sonication. This appears to indicate a strong embedding of the functionalised $Al_2O_3$ hydrophobic particles within the epoxy resin.

EXAMPLES 10 TO 14

Bonding of the functionalised $Fe_3O_4$ particles and the polymeric film by an epoxy resin was studied in examples 10 to 14. The polymeric film was coated with a mixture of the epoxy resin and the functionalised $Fe_3O_4$ particles described in Example 2. In these examples, epoxy resin was added to the functionalised $Fe_3O_4$ particle suspension. Deposition of the mixture onto the polymeric film was performed through spray coating at ambient temperature, as described previously.

The functionalised $Fe_3O_4$ particle and epoxy resin ratios and the corresponding WCAs for the polymeric films of examples 10 to 14 are summarised in Table 2. Table 2 also shows the WCAs for the polymeric films after they have been sonicated in isopropanol for approximately ten minutes.

TABLE 2

Water contact angle (°) before and after sonication as a function of the ratio of functionalised $Fe_3O_4$ particles and epoxy resin.

| Example | Isostearate functionalised $Fe_3O_4$ particles:epoxy resin | Water contact angle (°) | Water contact angle (°) after sonication |
|---|---|---|---|
| 10 | 11.8:1.0 | 124.3 ± 10.6° | 92.7 ± 8.3° |
| 11 | 6.5:1.0 | 102.1 ± 4.3° | 85.3 ± 14.5° |
| 12 | 2.0:1.0 | 89.9 ± 4.7° | 84.4 ± 5.9° |
| 13 | 1.0:1.0 | 75.4 ± 2.2° | 81.4 ± 3.0° |
| 14 | 1.0:1.5 | 80.7 ± 10.8° | 81.8 ± 2.5° |

When compared with Examples 5 to 9, the WCAs of Examples 10 to 14 are not as high. However, there is a clear trend that the WCA increases when increasing the ratio of functionalised $Fe_3O_4$ particles to epoxy resin. Therefore, it is plausible that the WCA could exceed 140° in embodiments where the functionalised $Fe_3O_4$ particle to epoxy resin ratio exceeds 15.0:1.0.

Figure 4:
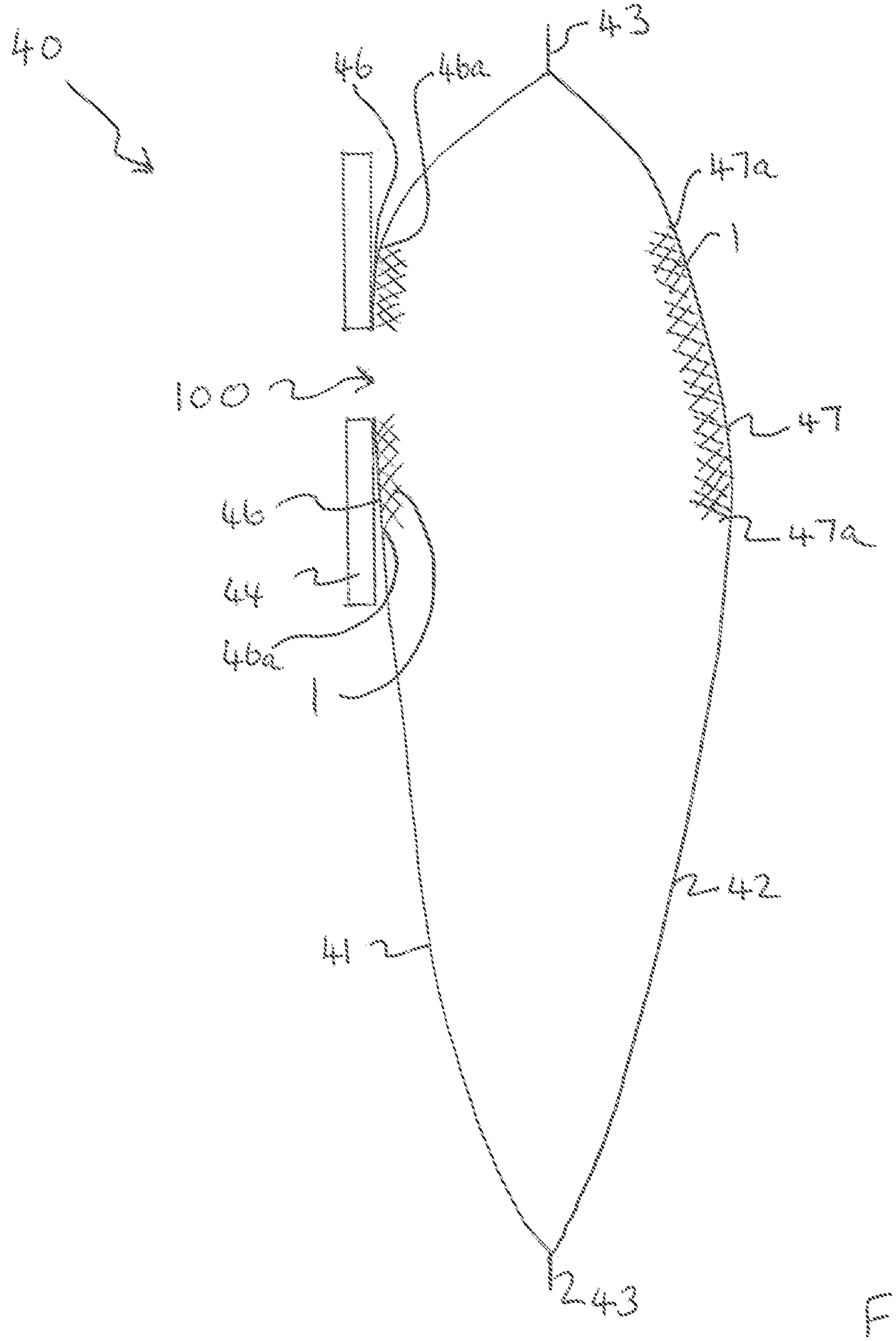
FIG. 4 is a cross sectional view of an ostomy pouch according to a first embodiment of the invention.

Referring now to FIG. 4 there is shown an ostomy pouch, indicated generally at 40, having a pair of opposed side walls 41, 42. The ostomy pouch 40 shown in this figure is of the closed-end type. The side walls 41, 42 are formed of a polymeric film, such as a polymeric film composed of any suitable heat-sealable plastic or a combination of plastics (e.g., as a coextruded laminate) that is tough, flexible, and liquid and gas impermeable. In some embodiments, the side walls 41, 42 may be separate pieces of film bonded (e.g. welded) at their respective edges 43. In other embodiments, the side walls 41, 42 may be formed from a single piece of film.

One of the side walls 41 defines a stoma-receiving opening 100 for, in use, receiving a part of a stoma (not shown) into the ostomy pouch 40. In some embodiments, the ostomy pouch 40 may comprise a wafer 44 for adhesively attaching the ostomy pouch 40 to the peristomal skin surfaces of a patient. The stoma-receiving opening 100 may have a diameter of from approximately 10 mm to approximately 50 mm to accommodate stoma having different sizes and shapes.

The ostomy pouch 40 is at least partially coated on an internal surface thereof (e.g. on an inner surface of one or both of the side walls 41, 42) with the hydrophobic particles 1. As described previously, the hydrophobic particles 1 comprise a metal oxide core 10 and a hydrocarbon chain 12 having from 2 to 40 carbon atoms. The hydrocarbon chain 12 is chemically bound to the metal oxide core 10. Any of the hydrophobic particles 1 disclosed herein could be utilised on the ostomy pouch 40.

In some embodiments, the side wall 41 defining the stoma-receiving opening 100 may comprise a first region 46 which surrounds the stoma-receiving opening 100. The first region 46 may have a peripheral edge 46a located approximately 40 mm from the centre of the stoma-receiving opening 100. Therefore, the distance across the first region 46 may be approximately 80 mm. The first region 46 may be coated with the hydrophobic particles 45.

In some embodiments, the first region 46 may only partially surround the stoma-receiving opening 100.

In some embodiments, the side wall 42 opposing the side wall 41 defining the stoma-receiving opening 100 may comprise a second region 47 which substantially faces the stoma-receiving opening 100 and is coated with the hydrophobic particles 1. The second region 47 may have a peripheral edge 47a and the distance across the second region 47 may be approximately 80 mm. Accordingly, the diameter of the second region 47 may be greater than the diameter of the stoma-receiving opening 100. The diameter of the second region 47 may also be approximately equal to the diameter of the first region 46. In some embodiments, the diameter of the second region 47 may be greater than or less than the diameter of the first region 46.

In some embodiments, the entire inner surface(s) of one or both side walls 41, 42 may constitute the respective first and second region(s) 46, 47. Accordingly, in some embodiments, the entire inner surface(s) of one or both side walls 41, 42 may be coated with the hydrophobic particles 1.

In use, body waste enters the ostomy pouch 40 from the stoma (not shown) via the stoma-receiving opening 100. As a consequence of the hydrophobic particles 1 present at the first and/or second region(s) 46, 47, and the high WCA thereof, substantial amounts of the body waste do not become attached to the side walls 41, 42 at or immediately adjacent the stoma-receiving opening 100. Instead, due to the self-cleaning nature of the hydrophobic particles 1, the body waste falls towards the bottom of the ostomy pouch 40. It has been found, particularly in relation to ostomy pouches of the closed-end type, that the phenomenon of pancaking is therefore substantially reduced. Accordingly, the adhesive of the wafer 44 does not become contaminated such that the wafer 44 detaches from the patient.

Figure 5:
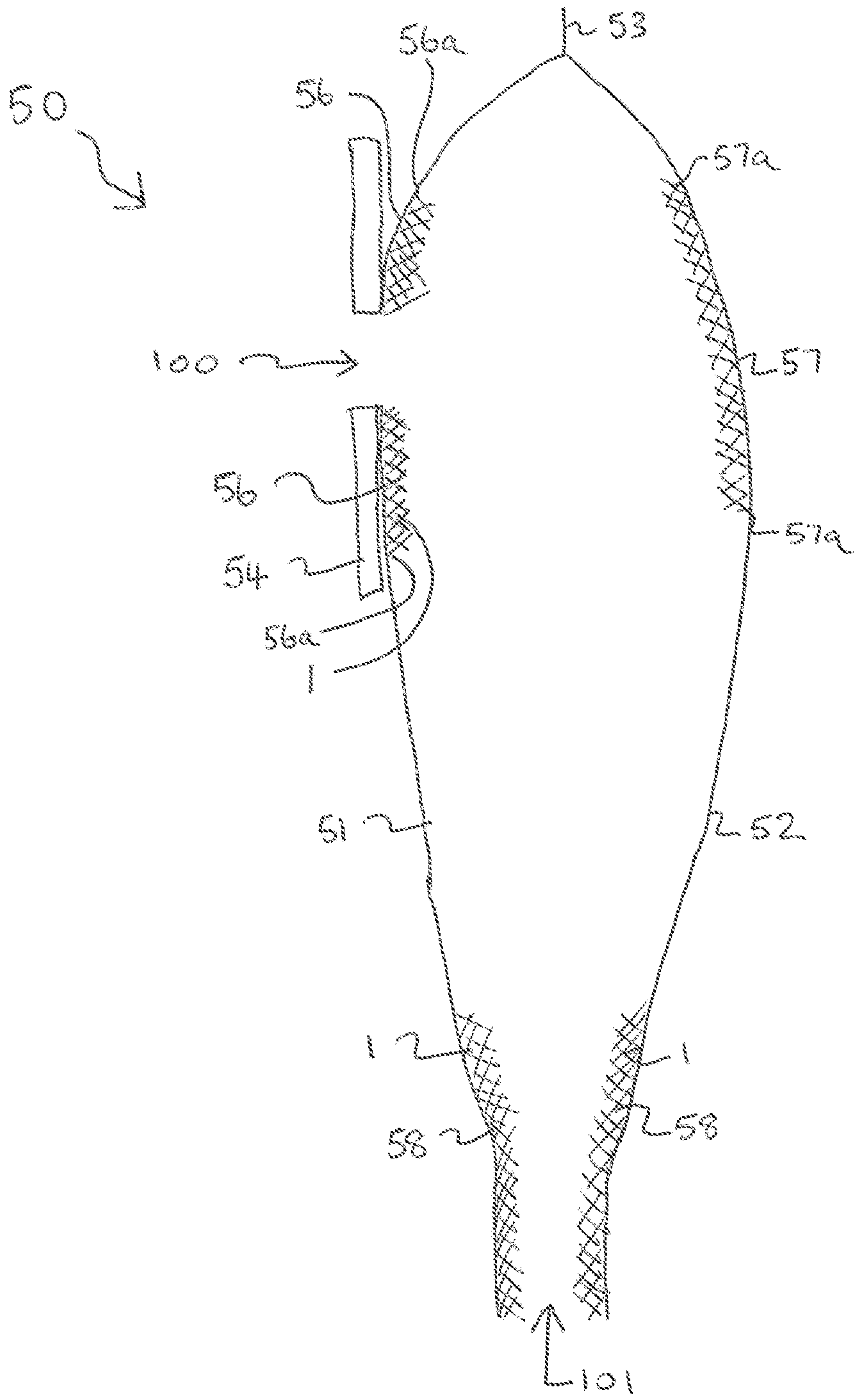
FIG. 5 is a cross sectional view of an ostomy pouch according to a second embodiment of the invention.

Referring now to FIG. 5 there is shown an ostomy pouch, indicated generally at 50. The ostomy pouch 50 shown in this figure is of the open-end type. Features of the ostomy pouch 50 that are common with the ostomy pouch 40 of FIG. 4 are denoted with a corresponding reference numeral in the 50s, rather than in the 40s. For instance, the side walls of the ostomy device 50 are denoted with reference numerals 51, 52, rather than 41, 42.

Embodiments of open-end type pouches may comprise a drainable opening, indicated generally at 101, at a lower end of the ostomy pouch 50 for drainage thereof. In some embodiments, the side walls 51, 52 may comprise a third region 58 which surrounds the drainable opening 101 and is coated with the hydrophobic particles 1.

In some embodiments the drainable opening 101 may be opened and closed using retaining means (not shown), such as a retaining clip or a hook and loop fastener. In such embodiments, the drainable opening 101 is typically closed by folding the side walls 51, 52 around one another and opened by reversing the action. In other embodiments the drainable opening 101 may be fitted with a valve (not shown). The internal surface of the valve may be coated with the hydrophobic particles 1.

Due to the high WCA of the hydrophobic particles 1 it has been found that the drainable opening 101 cleans itself of body waste. Accordingly, the drainable opening 101 is less likely to become clogged which can prolong the life of the ostomy pouch 50 and/or improve the hygiene thereof.

In some embodiments of the open-end type ostomy pouch 50, one or both of the first and/or second region(s) 56, 57 coated in the hydrophobic particles 1 may not be present. Accordingly, the hydrophobic particles 1 may be present only at the third region 58.

Figure 6:
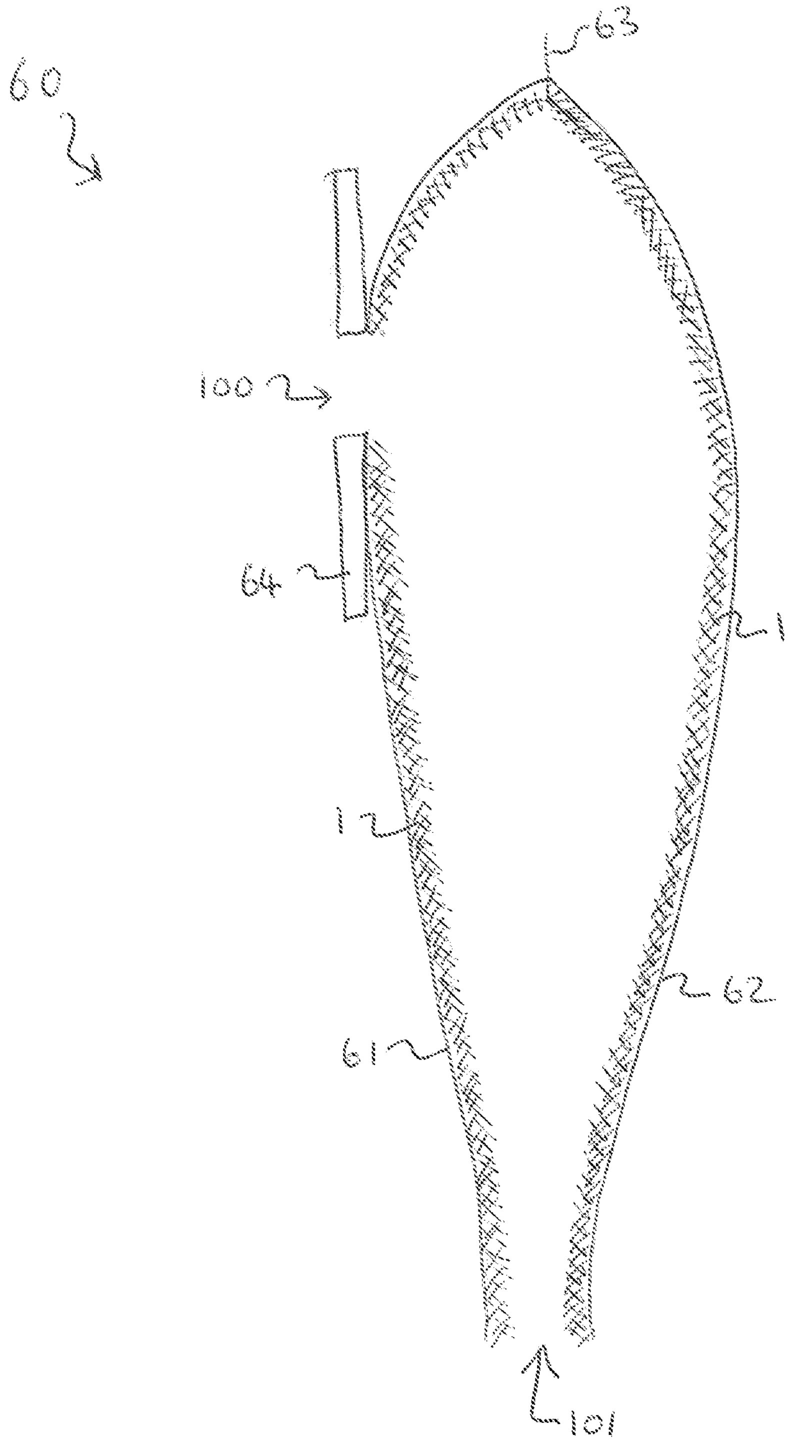
FIG. 6 is a cross sectional view of an ostomy pouch according to a third embodiment of the invention.

Referring now to FIG. 6 there is shown an ostomy pouch, indicated generally at 60. The ostomy pouch 60 shown in this figure is of the open-end type. Features of the ostomy pouch 60 that are common with the ostomy pouch 40 of FIG. 4 are denoted with a corresponding reference numeral in the 60s, rather than in the 40s. For instance, the side walls of the ostomy device 60 are denoted with reference numerals 61, 62, rather than 41, 42.

The entire internal surfaces of the side walls 61, 62 are coated with the hydrophobic particles 1 in ostomy pouch 60 of FIG. 6. However, ostomy pouches of a closed-end type could also be configured with the entire internal surfaces coated with the hydrophobic particles, without departing from the scope of the invention.

An advantage of coating the entire internal surfaces of an ostomy pouch with the hydrophobic particles is that the ostomy pouch is generally easier to clean.

In summary, the present invention relates to ostomy pouches 40, 50, 60 formed from polymeric films that have improved self-cleaning properties by virtue of attaching hydrophobic particles 1 thereto. It has been found that the surface energies of these polymeric films are very low and that the polymeric films are non-toxic. Accordingly, not only are the ostomy pouches 40, 50, 60 improved in terms of their self-cleaning properties but they are also improved because they are non-toxic. It is also clear that the adherence of the hydrophobic particles 1 to polymeric films is improved when compared to prior art solutions. Therefore, it is understood that the ostomy pouches 40, 50, 60 of the present invention will be longer lasting, specifically in terms of their hydrophobic nature.

It may be useful to tune the WCA at different regions of the ostomy pouch 40, 50, 60. In some embodiments, the WCA of any one of the first region 46, 56, the second region 47, 57 or the third region 58 may differ from another region. One way in which this can be achieved is by varying the concentration of hydrophobic particles that are deposited at the different regions. For instance, a solution of 4 wt % of $Al_2O_3$ hydrophobic particles may be deposited at the first and second regions 46, 56; 47, 57 and a solution of 2 wt % $Al_2O_3$ hydrophobic particles may be deposited at the third region 58. Accordingly, the first and second regions 46, 56; 47, 57 will have a higher WCA than the third region 58 due to the high concentration of $Al_2O_3$ hydrophobic particles.

As used herein, the term "hydrocarbon chain" is intended to have its usual meaning, i.e. a molecule that consists entirely of hydrogen and carbon.

Representative features are set out in the following clauses, which stand alone or may be combined, in any combination, with one or more features disclosed in the text and/or drawings of the specification.

When used in this specification and claims, the terms "comprises" and "comprising" and variations thereof mean that the specified features, steps or integers are comprised. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

Although certain example embodiments of the invention have been described, the scope of the appended claims is not intended to be limited solely to these embodiments. The claims are to be construed literally, purposively, and/or to encompass equivalents.

The invention claimed is:

1. An ostomy pouch having a pair of opposed side walls, one of the side walls defining a stoma-receiving opening for, in use, receiving a part of a stoma, one or both of the side walls being formed of a polymeric film at least partially coated on an internal surface thereof with adhered hydrophobic particles, the hydrophobic particles comprising:

an iron oxide core; and a hydrocarbon chain having from 2 to 40 carbon atoms, wherein each of the hydrophobic particles is spherical, wherein the hydrophobicity of the polymeric film is tuned at different regions across the internal surface such that a first region of the polymeric film has an associated first water contact angle measurement and a second region of the polymeric film has an associated second water contact angle measurement which differs from the first water contact angle measurement, wherein the first and second regions of the polymeric film are each coated with the hydrophobic particles, and wherein the hydrocarbon chain is covalently bound to the iron oxide core via a functional group, the functional group comprises any one or a combination of carboxylate, phosphinate, thiolate and/or thiocarboxylate.

2. An ostomy pouch according to claim 1, wherein the side wall defining the stoma-receiving opening is formed of the polymeric film and comprises the first region which at least partially surrounds or surrounds the stoma-receiving opening.

3. An ostomy pouch according to claim 2, wherein the side wall opposing the side wall defining the stoma-receiving opening is formed of the polymeric film and comprises the second region which substantially faces the stoma-receiving opening.

4. An ostomy pouch according to claim 3, wherein the diameter of the second region is greater than the diameter of the stoma-receiving opening.

5. An ostomy pouch according to claim 3, wherein the diameter of the second region is equal to the diameter of the first region.

6. An ostomy pouch according to claim 1, further comprising a drainable opening at a lower end thereof, both side walls being formed of the polymeric film and comprising a third region which surrounds the drainable opening, wherein the third region is coated with the hydrophobic particles.

7. An ostomy pouch according to claim 6, wherein the drainable opening includes a valve, optionally wherein the internal surface of the valve is coated with the hydrophobic particles.

8. An ostomy pouch according to claim 1, wherein both side walls are formed of the polymeric film and the entire internal surfaces thereof are coated with the hydrophobic particles.

9. An ostomy pouch according to claim 1, wherein the average diameter of the hydrophobic particles is less than or equal to 200 nm; or wherein the average diameter of the hydrophobic particles is less than or equal to 50 nm; or wherein the average diameter of the hydrophobic particles is from 8 nm to 20 nm.

10. An ostomy pouch according to claim 1, wherein the hydrocarbon chain is aliphatic.

11. An ostomy pouch according to claim 1, wherein the hydrophobic particles are free from fluorine.

12. An ostomy pouch according to claim 1, wherein the polymeric film comprises a thermoplastic film.

13. An ostomy pouch according to claim 12, wherein the thermoplastic film comprises polyolefin, vinyl polymer or polyacetal film.

14. An ostomy pouch according to claim 12, wherein the thermoplastic film comprises a co-extruded bilayer or multilayer film.

15. An ostomy pouch according to claim 1, wherein the hydrophobic particles are at least partially embedded in the polymeric film.

16. An ostomy pouch according to claim 1, wherein the hydrophobic particles and the polymeric film are secured to one another by an adhesive.

17. An ostomy pouch according to claim 16, wherein the mass ratio of the hydrophobic particles and the adhesive is from 1.0:1.0 to 2.0:1.0.

18. An ostomy pouch having a pair of opposed side walls, one of the side walls defining a stoma-receiving opening for, in use, receiving a part of a stoma, one or both of the side walls being formed of a polymeric film at least partially coated on an internal surface thereof with adhered hydrophobic particles, the hydrophobic particles comprising:

an iron oxide core;

a hydrocarbon chain having from 2 to 40 carbon atoms, and wherein the hydrocarbon chain is covalently bound to the iron oxide core via a functional group, the functional group comprises any one or a combination of carboxylate, phosphinate, thiolate and/or thiocarboxylate.

19. An ostomy pouch according to claim 1, wherein the hydrocarbon chain is branched.

* * * * *